United States Patent
Buja

(10) Patent No.: US 8,986,205 B2
(45) Date of Patent: Mar. 24, 2015

(54) SENSOR FOR MEASUREMENT OF TEMPERATURE AND PRESSURE FOR A CYCLIC PROCESS

(76) Inventor: Frederick J. Buja, Rochester, NY (US)

(*) Notice: Subject to any disclaimer, the term of this patent is extended or adjusted under 35 U.S.C. 154(b) by 238 days.

(21) Appl. No.: 13/108,906

(22) Filed: May 16, 2011

(65) Prior Publication Data

US 2011/0282163 A1 Nov. 17, 2011

Related U.S. Application Data

(60) Provisional application No. 61/334,828, filed on May 14, 2010.

(51) Int. Cl.
| | |
|---|---|
| *A61B 5/00* | (2006.01) |
| *G06F 15/00* | (2006.01) |
| *G01K 13/00* | (2006.01) |
| *A61B 5/01* | (2006.01) |
| *B29C 43/58* | (2006.01) |
| *A61B 5/0205* | (2006.01) |
| *A61B 5/021* | (2006.01) |
| *G01K 7/02* | (2006.01) |
| *G01K 7/00* | (2006.01) |
| *B29C 43/00* | (2006.01) |

(Continued)

(52) U.S. Cl.
CPC . *A61B 5/01* (2013.01); *B29C 43/58* (2013.01); *A61B 5/02055* (2013.01); *A61B 5/021* (2013.01); *G01K 7/02* (2013.01); *G01K 13/002* (2013.01); *B29C 2043/5808* (2013.01); *B29C 2043/5816* (2013.01); *G01K 2211/00* (2013.01); *A61B 5/024* (2013.01); *A61B 5/026* (2013.01); *A61B 5/681* (2013.01); *A61B 5/682* (2013.01); *A61B 2562/0247* (2013.01); *A61B 2562/0271* (2013.01)
USPC .......................................................... 600/300

(58) Field of Classification Search
CPC ........... G01K 7/02; G01K 5/48; G01K 5/486; G01K 7/021–7/028; G01K 7/04; G01K 7/06; G01K 2211/00; G01L 9/0001–9/0005; B29C 43/58

See application file for complete search history.

(56) References Cited

U.S. PATENT DOCUMENTS

| | | | | |
|---|---|---|---|---|
| 3,049,012 | A | * 8/1962 | Daniels | ......................... 374/179 |
| 3,314,129 | A | 4/1967 | Pugh et al. | |
| 3,332,286 | A | * 7/1967 | Strong | ............................ 73/755 |

(Continued)

FOREIGN PATENT DOCUMENTS

| | | |
|---|---|---|
| CA | 2274308 | 4/2005 |
| CA | 2427832 | 1/2008 |

(Continued)

OTHER PUBLICATIONS

Morgan, E. S. "The effect of stress on the thermal e.m.f. of platinum-platinum/13% rhodium thermocouples", 1968, J. Phys. D: Appl. Phys. 1, 1421-1429.*

(Continued)

*Primary Examiner* — William Thomson
*Assistant Examiner* — Marie Archer
(74) *Attorney, Agent, or Firm* — Duane C. Basch; Basch & Nickerson LLP

(57) ABSTRACT

Disclosed is a multi-variable sensor and systems and methods for its use to sense process changes or variations. The sensor is employed to concurrently sense a plurality of parameters (e.g., temperature and pressure) for a process.

12 Claims, 5 Drawing Sheets

(51) Int. Cl.
*A61B 5/024* (2006.01)
*A61B 5/026* (2006.01)

(56) References Cited

U.S. PATENT DOCUMENTS

| | | |
|---|---|---|
| 3,867,205 A | 2/1975 | Schley |
| 3,942,242 A | 3/1976 | Rizzolo |
| 4,018,624 A | 4/1977 | Rizzolo |
| 4,191,194 A | 3/1980 | Watanabe |
| 4,493,564 A | 1/1985 | Epstein |
| 4,527,005 A | 7/1985 | McKelvey et al. |
| 4,579,002 A | 4/1986 | Zettler |
| 4,681,099 A | 7/1987 | Sato et al. |
| 4,705,498 A | 11/1987 | Goss |
| 4,715,221 A | 12/1987 | Grims et al. |
| 4,721,589 A | 1/1988 | Harris |
| 4,816,197 A | 3/1989 | Nunn |
| 4,848,147 A | 7/1989 | Bailey et al. |
| 4,850,217 A | 7/1989 | Nunn |
| 4,932,250 A | 6/1990 | Assaf et al. |
| 4,983,336 A | 1/1991 | Langlois |
| 4,990,193 A * | 2/1991 | Kimura .................. 136/201 |
| 5,043,023 A | 8/1991 | Bentley |
| 5,069,222 A | 12/1991 | McDonald, Jr. |
| 5,158,366 A | 10/1992 | Nagai et al. |
| 5,205,293 A | 4/1993 | Ito et al. |
| 5,320,513 A | 6/1994 | Schmidt |
| 5,419,858 A | 5/1995 | Hata et al. |
| 5,502,292 A | 3/1996 | Pernicka et al. |
| 5,520,461 A | 5/1996 | Curry |
| 5,665,283 A | 9/1997 | Bader et al. |
| 5,705,659 A | 1/1998 | Park et al. |
| 5,707,659 A | 1/1998 | Erikson |
| 5,735,280 A | 4/1998 | Sherman et al. |
| 5,772,933 A | 6/1998 | Kotzab |
| 5,832,592 A | 11/1998 | Bowman et al. |
| 5,902,252 A | 5/1999 | Hohlfeld et al. |
| 5,937,853 A | 8/1999 | Strom |
| 5,945,046 A | 8/1999 | Hehl et al. |
| 5,959,195 A | 9/1999 | Gottfert |
| 5,980,237 A | 11/1999 | Swenson et al. |
| 5,989,192 A | 11/1999 | Weijand et al. |
| 5,993,704 A | 11/1999 | Bader et al. |
| 6,006,601 A | 12/1999 | Osborne |
| 6,077,228 A | 6/2000 | Schonberger |
| 6,077,470 A | 6/2000 | Beaumont |
| 6,084,174 A | 7/2000 | Hedengren et al. |
| 6,090,318 A | 7/2000 | Bader et al. |
| 6,293,700 B1 | 9/2001 | Lund et al. |
| 6,312,628 B1 * | 11/2001 | Wieder et al. ............. 264/37.27 |
| 6,393,919 B1 * | 5/2002 | Ohji et al. ............. 73/708 |
| 6,464,909 B1 | 10/2002 | Kazmer et al. |
| 6,503,438 B2 | 1/2003 | Beaumont et al. |
| 6,579,242 B2 | 6/2003 | Bui |
| 6,649,095 B2 | 11/2003 | Buja |
| 6,862,932 B2 | 3/2005 | Zimmermann et al. |
| 2,274,308 A1 | 4/2005 | Godwin et al. |
| 7,050,846 B2 | 5/2006 | Sweeney et al. |
| 7,051,120 B2 | 5/2006 | Greene et al. |
| 7,052,456 B2 | 5/2006 | Simon |
| 7,055,520 B2 | 6/2006 | Swisa |
| 7,060,030 B2 | 6/2006 | Von Arx et al. |
| 7,062,327 B2 | 6/2006 | Bradley et al. |
| 7,063,669 B2 | 6/2006 | Brawner et al. |
| 7,064,270 B2 | 6/2006 | Marshall et al. |
| 7,065,396 B2 | 6/2006 | Hampton |
| 7,065,409 B2 | 6/2006 | Mazar |
| 7,128,714 B1 | 10/2006 | Antonelli et al. |
| 7,181,264 B2 | 2/2007 | Wiesmann et al. |
| 7,278,937 B2 | 10/2007 | Laliberty et al. |
| 7,585,166 B2 | 9/2009 | Buja |
| 7,985,185 B2 | 7/2011 | De Voir et al. |
| 2002/0097155 A1 | 7/2002 | Cassel |
| 2004/0170213 A1 | 9/2004 | Rund et al. |
| 2004/0185142 A1 | 9/2004 | Olaru |
| 2005/0277872 A1 | 12/2005 | Colby |
| 2006/0206029 A1 | 9/2006 | Yair |
| 2006/0246167 A1 | 11/2006 | Buja |
| 2008/0039739 A1 | 2/2008 | Buja |
| 2008/0081963 A1 * | 4/2008 | Naghavi et al. ............. 600/301 |

FOREIGN PATENT DOCUMENTS

| | | |
|---|---|---|
| WO | WO0236326 | 5/2002 |
| WO | WO2008022122 | 2/2008 |

OTHER PUBLICATIONS

Baldes, E.J. "Micromethod for measuring Osmotic Pressure"; 1934; J. Sci. Instrum. 11, 223-225.*
Birch, F. "Thermoelectric Measurement of High Temperatures in Pressure Apparatus", Rev. Sci. Instrum. 10, 137-140, (1939).*
Bloch, F. et al. "Effect of Pressure on emf of Thermocouples", J. Appl. Phys. 38, 409-412 (1967).*
Hanneman, R. E. and Strong, H. M. "Pressure Dependence of the emf of Thermocouples to 1300°C. and 50 kbar"; J. Appl. Phys. 36, 523-528 (1965).*
Waxman, M and Hastings, R. J.; "Proposed Experiment to Determine the Effect of Pressure on the emf of Thermocouples"; J. Appl. Phys. 43, 2629-2632 (1972).*
Zanstra, P. E. "Welding uniform sized thermocouple junctions from thin wires"; 1976 J. Phys. E: Sci. Instrum. 9, 526-528.*
Bundy, F. P, "Effect of Pressure on emf of Thermocouples", J. Appl. Phys. 32, 483-488 (1961).*
Eisner, A. D. "Design and Development of a Micro-Thermocouple Sensor for Determining Temperature and Relative Humidity Patterns within an Airstream": Journal of biomechanical Engineering; Nov. 1989, vol. 11; 283-287.*
10008083_6649095 The Prosecution History as of Jul. 21, 2011 for U.S. Appl. No. 10/008,083, filed Nov. 5, 2001, Published Jul. 4, 2002, As US 2002-0084543 A1; Issued Nov. 18, 2003 As US Patent 6,649,095; Inventor: Frederick J. Buja.
11381246_7585166 The Prosecution History as of Jul. 21, 2011 for U.S. Appl. No. 11/381,246, filed May 2, 2006, Published November 2, 2006, As US-2006-0246167-A1; Issued September 8, 2009 As US Patent 7,585,166; Inventor: Frederick J. Buja.
11838491 The Prosecution History as of July 21, 2011 for U.S. Appl. No. 11/838,491, filed August 14, 2007, Published February 14, 2008, As US- 2008-0039739-A1; Inventor: Frederick J. Buja.
Applebaum , A. et al.; Correlation of blood temperature fluctuations with blood pressure waves,Basic research in cardiology 77 , 93 to 99 (S 1982).
Buja, F.J.; Establishing the molding Process and Molded Product "Consistency"; Revised Jun. 1990; Presented last by F.J. Buja in Chicago at National Plastics Expo, Jun. 1994 p. 1-43.
Buja, F.J.; Establishing the molding Process and Molded Product "Consistency"; Revised Jun. 1990; Presented last by F.J. Buja in Chicago at National Plastics Expo, Jun. 1994 p. 44-101.
Buja, F.J.; Using Mold Opening to Relate the Molding Process to Molded Product; KTechnologies c. 1986.
Digital Optics Corporation; Standard Processes Oct. 19, 2004; Process Specification Sheet; 1 page; Digital Optics Corporation, 8701 Mallard Creek Road, Charlotte, NC 28262, USA; 704-549-5556.
Dynisco; Heaterless Injection machine Nozzles; Dynisco Instruments; www.dynisco.com.
Dynisco; Technical Reference; "Using Pressure Transducers to Improve Control of the Extrusion Process"; pp. 170-174.
Kistler; Nozzle Pressure Measuring Chain for Injection Molding Machines.
Kistler; P-T Sensor for Molding Cavity Pressure and Temperature.
Koelsch, J.R., Contributing Editor; "Temperature control Builds Better Injection Molding"; Quality Magazine; May 2000; www.qualitymag.com/articles/2000/may00/0500f3.asp.
Love, A.; A treatise on the mathematical theory of the elasticity; fourth edition revised ; C.. 1927 ; 92 to 94 ; 117 ; 140 to 141 ; 146 to 151; ISBN 0-486 -60174 -9; Dover Publications, Inc., Mineola NY 11501.

(56) References Cited

OTHER PUBLICATIONS

Merck Manual, 18th Edition, Copyright 2006 by Merck & Co., pp. 2549-2550.

Nanmac; "Selecting the Right Thermocouple: There are more choices today"; Reprinted from Plastics Technology; Nanmac Corporation; www.nanmac.com; c. 1998.

Noral; Temperature Sensors for Industry; www.noraltemperaturesensor.com; Noral, Inc.

PCTUS2001046619_WO2002036326 International Preliminary Report on Patentability Dated Feb. 7, 2003 for PCT/US2001/046619 Filed Nov. 5, 2001, Published May 10, 2002, as WO/2002/036326; Inventor: Frederick J. Buja; Corresponding to US Patent 6,649,095.

PCTUS20070775894_WO2008022122 The International Preliminary Report on Patent Ability Date Feb. 17, 2009 for PCT/US2007/075894, Published February 21, 2008 as WO 2008/022122; Corresponding to U.S. Appl. No. 11/838,491; Inventor Frederick J. Buja.

Rosato, D.V. and Rosato, D.V.; Injection Molding Handbook; 2nd Edition; ISBN 0-412-99381-3; pp. 512-547 ; c. 1995 Chapman & Hall, New York, NY.

Rosato, D.V. and Rosato, D.V.; Injection Molding Handbook; 2nd Edition; ISBN 0-412-99381-3; pp. 548-580 ; c. 1995 Chapman & Hall, New York, NY.

Sheth, H.R.; Nunn, R.E.; An Adaptive Control Methodology for the Injection Molding Process, Part 2: Experimental Application; University of Massachusetts Lowell, Department of Plastics Engineering, Lowell MA 01854; Journal of Injection Molding Technology; Sep. 2001; vol. 5 No. 3; pp. 141-151.

Webster's II New Riverside University Dictionary, 1994 p. 159 and 749 regarding "bead"; p. 1190-1194 regarding "terminate".

\* cited by examiner

SENSOR FOR MEASUREMENT OF TEMPERATURE AND PRESSURE FOR A CYCLIC PROCESS

This application claims priority from U.S. Provisional Patent Application 61/334,828 for an IMPROVED SENSOR, filed May 14, 2010 by Frederick J. Buja, and from pending U.S. patent application Ser. No. 11/838,491 for a "SYSTEM AND METHOD EMPLOYING A THERMOCOUPLE FOR MONITORING OF PHYSIOLOGICAL PARAMETERS," filed Aug. 14, 2007, by Frederick J. Buja, which claims priority from U.S. Provisional Application 60/822,379 for a "SYSTEM AND METHOD FOR MONITORING OF PHYSIOLOGICAL PARAMETERS," filed Aug. 14, 2006 by Frederick J. Buja, all of the above are hereby incorporated by reference in their entirety.

A multi-variable sensor for use in various embodiments and configurations is disclosed. The sensor is employed to sense a plurality of parameters (e.g., temperature and pressure) for a process. In several disclosed applications the process is cyclical in nature and the responsiveness of the sensor is important relative to sensing small changes in the cycles, as well as the sensor's ability to concurrently provide a signal representative of at least temperature and pressure to which it is exposed.

COPYRIGHT NOTICE

A portion of the disclosure of this application document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND & SUMMARY

In various biological processes, there is a need to sense temperature and pressure associated with the processes. For example, in humans and other mammals it may be important to sense a body temperature as well as blood pressure. Other applications of temperature sensing include the detection of respiration, and respiration rate.

In one biological embodiment, the disclosed system and method may be used to sense temperature and pressure of a specimen (e.g., a mammal) in a physiological setting. Such sensing may be accomplished through non-invasive and/or invasive techniques. In those situations where direct exposure of the thermocouple junction is not possible, the junction may be encapsulated in a flexible, thermally-conductive covering so as not to impede the sensing of pressure and temperature variations it is intended to sense. It should be appreciated that a thermocouple formed with a generally-spherical, micro-bead type junction may be employed to sense not only changes in temperature, but also localized changes in pressure. In such embodiments, the reduced-size, bead-shaped thermocouple junction is preferably exposed to the physiological environment or specimen it is intended to sense in order to reliably provide a signal response to changes in temperature and/or pressure. As discussed herein, the response of the micro-bead thermocouple (e.g., a bead formed by welding of thin thermocouple wires, made from iron, and constantan or other known thermocouple combinations, is capable of sensing both temperature and pressure components.

For example, the sensor is contemplated as a pulse sensor, where the sampling frequency or resolution (response time of sensor and associated analog-to-digital interface) must be fast enough to permit accurate sensing of the analog output curve to represent physiological parameters such as a pulse. In such an embodiment, the response time and sampling rate of the sensor and associated electrical circuitry must be less than the maximum pulse rate to be sensed. At a minimum the sampling rate should be one half the maximum pulse rate to be sensed, but in order to assure higher accuracy, it is believed that sampling rates of one or more orders of magnitude greater than the maximum are preferred. Moreover, in order to use a thermocouple-based sensor, such systems may include a variable output threshold for sensing pulses.

In various industrial and man-made devices there is also a need to sense temperature and pressure associated with the process. And, aspects of the systems and methods disclosed herein are also applicable to such industrial processes. One such example is a molding process, wherein a part is molded using a material to fill a mold cavity. More specifically, the industrial process may include an injection or similar molding operation.

When the multi-variable sensor disclosed herein is to be employed in industrial processes such as material molding (e.g., injection molding), the sensor may be used to monitor and or control the industrial processes. In such embodiments, placement of the sensor, an exposed thermocouple bead, may be critical. Moreover, the location of the bead relative to the process (e.g., in the mold, in contact with melt material, in a vent, etc.) may be used to provide additional information on the process. Included in the following disclosure and figures are various examples and illustrations of the manner in which such sensors may be arranged and installed. Moreover, in the case of using the sensors in mold cavity vents, the sensors themselves may be laid out in an array of sensors and the output of the sensors used to control the molding process (e.g., control closing of a gate upon detection of cavity fill and pack). For example, the sensor leads may be placed in a vent slot in the mold, and held in place using a plug such that the sensor leads are placed into a "U" shapes and the sensor bead is exposed in the vent cavity to sense the air/gas being exhausted from the mold cavity. In a multi-cavity mold (e.g., 32 as illustrated in the following figures), an array of 32 vent sensors may be installed and monitored.

Disclosed in embodiments herein is a method for concurrently sensing a combined temperature and pressure of a process, comprising: sensing a plurality of cycles of the process using a micro-bead sensor in direct contact with an element of the process, including providing a sensor consisting of two dissimilar metal wires terminated by a generally-spherical, micro-bead junction suitable for exposure to the process; exposing the micro-bead junction to the process, where in the junction senses the process and produces a signal in response to the process; receiving the signal; converting the signal to data representing at least temperature and pressure using at least one reference point against which the sensor was calibrated; and at least temporarily, storing data representing the temperature and pressure in memory; wherein the sensing and receiving of the signal occurs at a rate less than one-half that of a period of the process cycle.

Also disclosed in embodiments herein is A system to measure at least temperature and pressure of a cyclic process, comprising: at least one generally spherical micro-bead sensor formed from dissimilar metals; electrical circuitry to receive a sensor output signal and convert the sensor output signal to a digital signal; a processor for receiving the digital signal and processing the received digital signal in order to quantify at least temperature and pressure components of the signal relative to at least one reference point against which the sensor was calibrated, the processor correcting for the reference point to produce an output representing at least two parameters.

Figure 3:
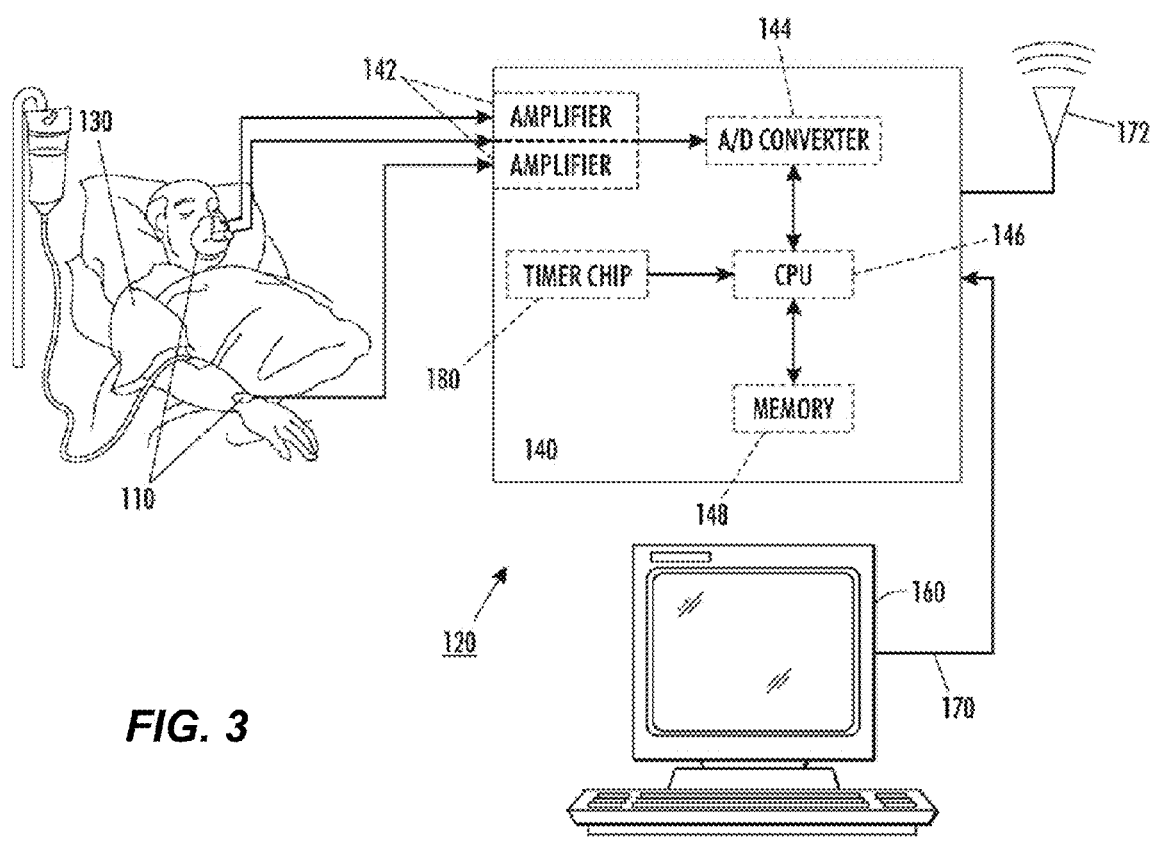
Figure 4A:
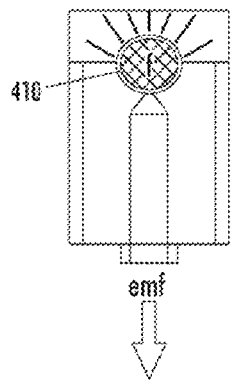
Figure 4B:
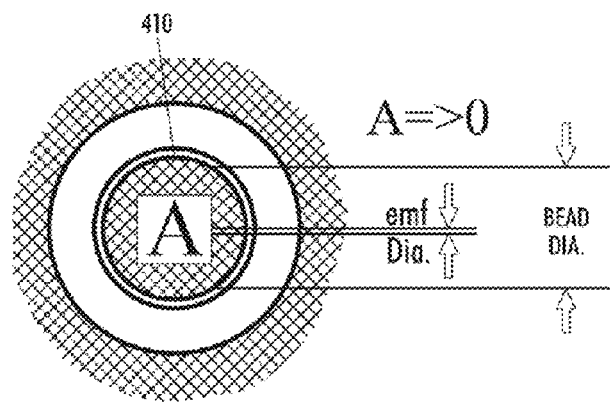
Figure 5:
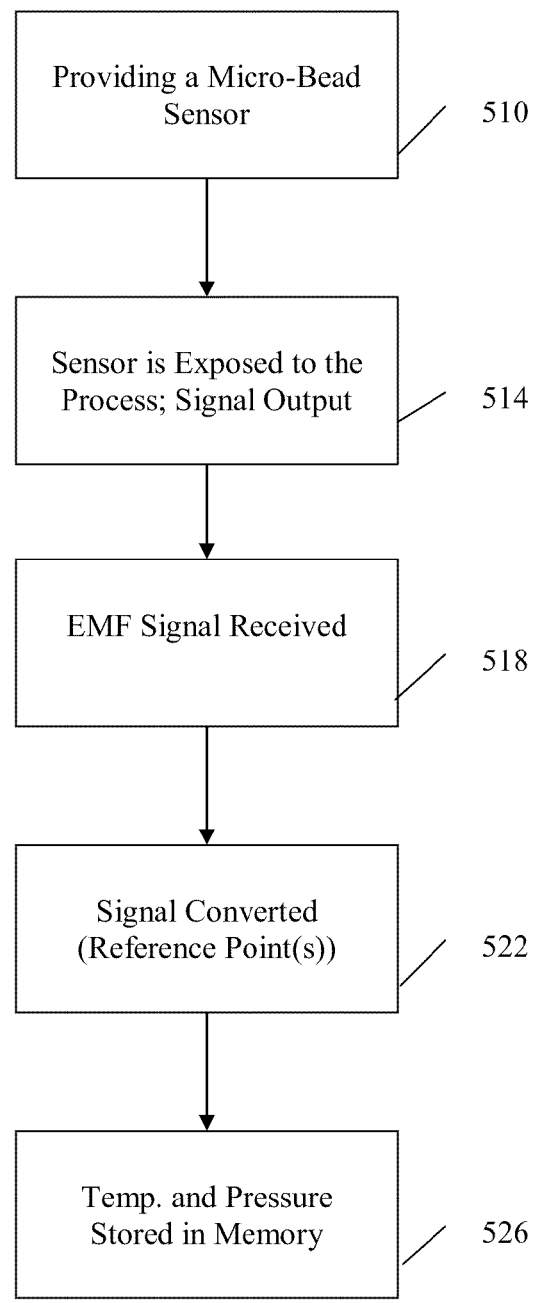

FIG. is an exemplary illustration of a system to measure at least temperature and pressure of a cyclic process;

FIG. 3 is a block diagram illustrating various components in a system for sensing physiological parameters;

FIGS. 4A and 4B are illustrations of a micro-bead sensor in accordance with the disclosed embodiments; and FIG. 5 is a general flow diagram illustrating operation sin a method for concurrently sensing a combined temperature and pressure of a process.

The various embodiments described herein are not intended to limit the embodiments described. On the contrary, the intent is to cover all alternatives, modifications, and equivalents as may be included within the spirit and scope of the invention as defined by the appended claims.

DETAILED DESCRIPTION

As noted above, the disclosed sensor and associated systems and methods are suitable for sensing at least the temperature and pressure variations related to a cyclic process. Moreover, the temperature and pressure variations may be sensed using a single, micro-bead junction formed from a combination of dissimilar metals. The junction is responsive to not only changes in temperature, but also to changes in pressure. More specifically, the electromotive force (emf) voltage that is generated by the junction of the dissimilar metals is the result of not only the temperature but also the pressure. In other words, the resulting emf is the sum of the emf due to the temperature of the junction ($T_{emf}$) plus the emf due to the pressure applied to the junction ($P_{emf}$). As a result the sensor finds particular use in the monitoring of various processes, including cyclic processes that are used in industrial settings and biological settings where changes in temperature and pressure are relevant to the process.

Figure 1:
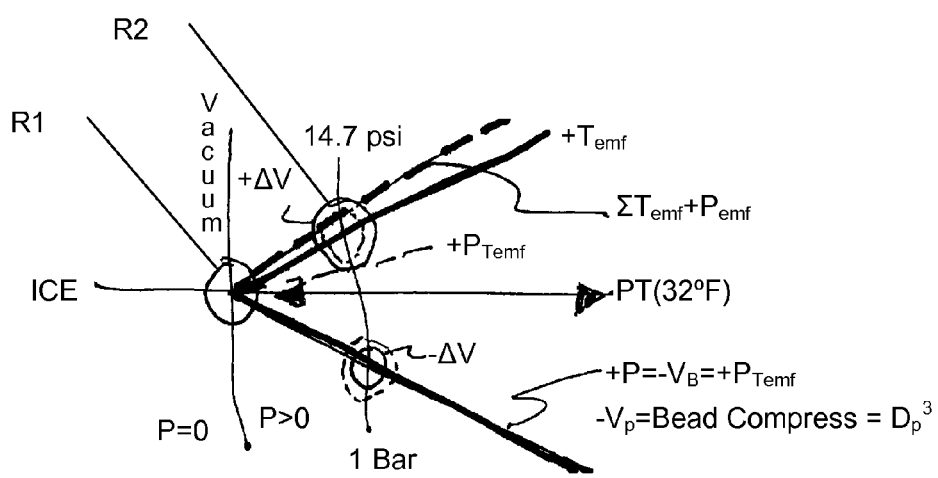
FIG. 1 is an illustration of the manner in which a reference point is employed to characterize the components of the sensor output.

Referring to FIG. 1, there is depicted a graphical representation of the use of at least one reference or calibration point (R1) to determine the contribution of the emf from both the temperature and pressure applied to the bead junction. In FIG. 1, the reference point is an ice-point, zero-vacuum reference. Under Temp.=0° C. and Press.=0 Bar., the emf voltage reading of the bead junction is obtained as a calibration point, and the data for the junction is converted to a value (relative to a reference voltage) and stored in a memory for later use as will be described below. Subsequently, by varying either the temperature or the pressure to which the bead is exposed, additional reference points (e.g., R2) can also be observed and recorded. Once the reference point(s) is determined, then subsequent readings of the emf output by the bead junction can be broken into component parts to determine changes in both temperature ($T_{emf}$) and pressure ($P_{emf}$) relative to the reference point (R1). As further illustrated in FIG. 1, the response of the bead is dependent upon the bead size and the relative coefficients of expansion and material modulii for the dissimilar metals. As indicated relative to point P, the resulting emf is the sum of the emf contributed by a temperature change ($\Delta T$) and a pressure change ($\Delta P$), resulting in the sum ($\Sigma = T_{emf} + P_{emf}$) as shown by the upper dashed line.

Figure 2:
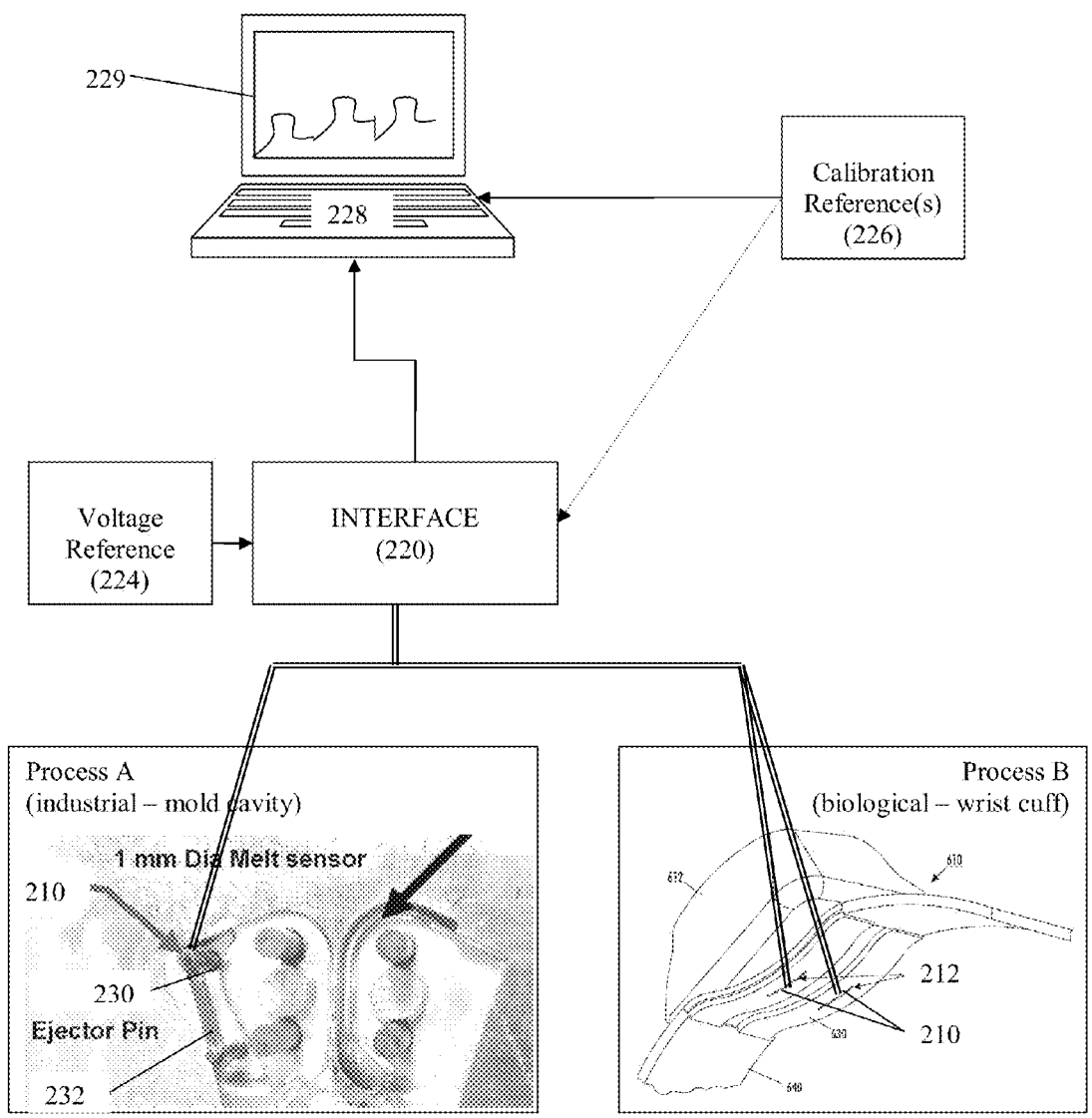

A system to measure at least temperature and pressure of a cyclic process is depicted in FIG. 2. System 200 comprises at least one generally spherical micro-bead sensor 210 formed from dissimilar metals such as iron and constantan (Cu—Ni alloy), although other material combinations are also known to produce an emf response. In the biological embodiment, sensors 210 may be placed individually on the surface of or internal to a living organism. As illustrated in the figure, one embodiment is a generally linear array of sensors 212, that, when used in conjunction with other spaced-apart sensors may be able to detect blood flow rate as well as temperature and pressure variations of the specimen. It will also be appreciated that, as depicted in FIG. 3, the sensor may be employed to sense temperature changes due to respiration, and may also be enclosed in or associated with a catheter or similarly invasive instrument such that the temperature and pressure may be detected internal to an organism. In the alternative, industrial, embodiment the exposed micro-bead junction is inserted through an ejector pin 230 into a mold cavity 232. There the exposed bead comes into contact with the material being molded during the molding cycle.

Although depicted relative to an ejector pin, the use of such sensors in other portions of molds and industrial equipment is also contemplated. For example, the manufacturing process employing a mold may have the sensor applied at any one or a combination of the following: a mold cavity vent; in contact with the material being molded; an aperture through which molding material flows; a mold flow controlling mechanism; an ejector pin; a mold cavity; a stationary pin; machine nozzle retaining hole; and a mold cavity plate. In other industrial processes, such as heat-treating or similar ovens, environmental test chambers and the like, the micro-bead sensors may be attached to a surface to be monitored, or they may be mounted so as to extend into an open atmosphere to assure an accurate and responsive measurement of the ambient temperature and pressure of the atmosphere with in such ovens and chambers.

In the various applications, electrical circuitry such as an interface 220 is used to receive the sensor output signal (emf voltage) and convert the sensor output signal to a digital signal. In one embodiment an A-to-D converter may be used in association with a reference voltage 224, to produce a digital output. It will be further appreciated that the interface itself includes some capability for regularly or periodically sampling the signals and at least the temporary storage of the signals, prior to sending the signals, or the digital representation thereof, for further processing or display on a computer platform 228 or similar display/output device (e.g., screen 229). In one embodiment, the interface or the computer receiving the digital signal and processes the received digital signal in order to quantify at least temperature and pressure components of the signal. This is done in conjunction with stored reference or calibration point(s) 226, where the processor uses at least one reference point against which the sensor was calibrated, and the processor corrects for the sensor emf at the reference point to produce an output representing both temperature and pressure as described relative to FIG. 1. More specifically, the system employs a processor (e.g., computer 228) and the at least one reference point, to produce a first output representing a digital temperature change ($T_{emf}$) and a pressure change ($P_{emf}$) due to bead compression, where the combination of the temperature change and pressure change from the at least one reference point are determined.

An alternative biological sensing embodiment is depicted in FIG. 3. Referring to FIG. 3, there is depicted a block diagram of a physiological sensor 110 in a monitoring system 120 for a human 130. The sensor includes at least one thermocouple having a bead-shaped junction suitable for exposure to a physiological process(es), whereby the junction can sense a physiological parameter, the thermocouple producing a signal in response to the physiological parameter such as the specimen's temperature, pulse rate, etc. The sensor provides an output signal from the thermocouple junction in the form of a voltage ($V_{emf}$), that is passed to circuitry 140 for processing. In one embodiment, the circuitry may include an amplifier(s) 142 for amplifying the emf voltage ($V_{emf}$), and an analog-to-digital (ND) converter 144 for converting the $V_{emf}$ to a digital value or representation. Under the control of a processor or CPU 146, the data is collected from the ND converter and at least temporarily stored in memory 148, and may be subsequently processed and transmitted, etc. As will be discussed relative to the processes described below, the processor 146 may perform various calculations to both adjust the readings as well as to provide desired physiological output For example, in addition to converting the voltage to a temperature, the system also corrects the temperature to a standard ambient condition (e.g. 14.7 psi pressure).

As also depicted in FIG. 1, system 120 may include one or more workstations, or similar handheld computing devices (e.g., Blackberry™, Palm Pilot™, iPOD™) that interface or at least receive the data from circuitry 140. In one embodiment, the workstation 160 may also provide programmatic control software to the processor 146 through wired 170 (direct serial, parallel, USB, network) or wireless 172 (infrared, radio frequency, Bluetooth™, etc.) communications means or links. Similarly, the workstation or handheld device may permit a user to control operation of the system, including the frequency of monitoring (continuous, periodic, based upon a trigger point, etc.), the amount of data to store (e.g., all, last five readings, etc.), the method for transmission of data, as well as specimen data (name, patient identification code, etc.). Although not depicted it will be appreciated that conventional interface components and circuitry may be employed to accomplish one or more alternative communications links within the system of with external devices to which the system may send physiological parameter data.

Relative to the workstations or handheld devices, it should be appreciated various instruments are suitable for receiving and/or displaying signals produced by one or more of the sensors described herein and logging or otherwise recording the signals. The instruments may further include the ability to display data that is representative of the signals (processed and unprocessed), e.g., over time—such as in the form of a time-based graph. As will be appreciated, it may be necessary to precondition or otherwise process the signals from the various sensing devices. For example, it may be necessary to provide amplification or similar processing in relation to the thermocouple signals generated.

Returning to the example of FIG. 3, the sensor may be used to monitor, via a thermocouple bead sensor 110 placed in or near the patient's mouth, the physiological parameter of body temperature. Here again, the circuitry stores data over a period of time to sense changes in temperature and to thereby represent a physiological process. In a further contemplated embodiment, the sensors 110 may be employed to sense temperature at a plurality of sites or locations in or on a specimen. And, as previously noted, the sensor may also be used within the specimen although depicted only in situations where it is attached to a specimen surface.

In summary, for either the industrial or the biological processes there is disclosed a system to measure a plurality of parameters (e.g., temperature and pressure), including at least one generally spherical microbead formed from dissimilar metals. The sensor is connected to an interface or similar I/O connection to receive the sensor output signal and convert the sensor output signal to a digital signal; and a processor then receives the digital signal and processes the received signal in order to quantify at least two parameters relative to at least one reference point, the processor correcting for the reference point to produce and store an output of the at least two parameters.

As depicted, for example in FIGS. 4A and 4B, the bead-shaped junction 410 is a micro-bead where the thermocouple senses changes in a thermo-mechanical response as an expansion/contraction from heat and compression/decompression of pressure exerted on the bead-shaped junction, thereby producing a signal including a pressure component. In other words, the response of the micro-bead junction includes an enhanced or amplified pressure response, from the response of the bead surface area, so that the pressure and temperature may both be sensed simultaneously. The sensor generates, through the micro-bead junction, a thermo-mechanical response that includes a response to an encompassing gas, liquid, or solid pressure fluctuation. It will be recognized that the micro-bead may be formed as a contact region between two dissimilar metal wires (e.g., iron and constantan) that produce a varying voltage in response to changes in temperature and pressure. Moreover, at least one of the dissimilar metal wires has a generally round cross-section. As illustrated in FIG. 4B, the contact is a fused or welded contact, preferably using a fusing source so as to minimize the size and inner core density (K) change of the thermocouple junction and the associated or surrounding bead. The response of the sensor bead to pressure (mechanical) variability is believed to be significantly enhanced by reducing the size of the bead. Thus, micro-beads having small diameters are believed preferable. Ranges of micro-bead diameters on the order of 0.10 inches and smaller are believed to be preferable, and micro-beads having sizes of about 0.001-0.010 may prove to provide highly suitable responses.

In one embodiment, the sensor employed for sensing pressure, temperature, etc. may be a sheathed sensor with a 0.060" diameter, which can be purchased from Omega, with stripped wire ends suitable for welding. The thermocouple is preferably formed with a micro-bead junction, wherein the smaller the bead size, the more sensitive the junction is to changes at the bead surface to temperature and pressure, etc. More specifically, the response of the micro-bead junction is a combination of the temperature and pressure fluctuation acting as work energy on the emf junction. The strain of the spherical bead is directed to the emf junction. As a further illustrative example, consider a bead surface area change from MEAN Diameter=Pi·$D^2 \pm \Delta D$. The area Increase is not equal to the change from nominal by the factor+2 $\Delta D^2$ or $(D \pm \Delta D)^2$, where $(D+\Delta D)^2 = 2D^2 + 2\Delta D + \Delta D^2$ and $(D-\Delta D)^2 = 2D^2 - 2\Delta D + \Delta D^2$. Rather the area is smaller by the same that the $\pm 2\Delta D$ factor, but the smaller area is less by a $+\Delta D^2$ exponential ratio, thereby leading to force concentration and responsiveness to pressure variations. Where the junction size decreases from compression of the bead, the pressure sensed on the junction of the thermocouple is effectively increased, wherein the traditional thermocouple junction further becomes sensitive to pressure changes as well as temperature changes, and can produce signals indicative thereof. In other words, the micro-bead junction is believed to produce a significant emf response to both changes to temperature as well as pressure.

Considering the thermal-mechanical response of the micro-bead thermocouple, the response may be predicted in terms of thermal-mechanical flex ($_BZ$) in relation to the illustrations found in FIGS. 4A-B.

$$_BZ_{eE} = {_BT_e} \cdot {_BM_E};$$

$$\Delta_B L_E / \pi (\text{Spherical Bead}) = \Delta_B D_E;$$

$$_A F_{G,L,S} = {_A P_{G,L}} \cdot {_{SB}A_{E0}}, \text{ representing applied bead surface force}$$

$$_BZ = [_B CD_{eE@T=0} + (_B mD_{eE} \cdot {_BT_{eactual}})] \cdot [(_B D_{E0} \cdot {_A F_{G,L,S}}) / (_B A_{E0} \cdot {_B D_E})];$$

$$_BZ = [_B C_{eE@T=0} + (_B m_{eE} \cdot {_B T_{eactual}})] \cdot [(_A P_{G,L,S} \cdot {_B D_{E0}}) / (_B D_E)];$$

$$_A F_{G,L,S} = {_A P_{G,L,S}} \cdot {_B A_{E0}}$$

$_B K_{eE}$ = Bulk Modulus #/In$^3$ Volume = FORCE on Bead; where matter D is bead diameter, state $(_A)={_A}$G=Gas, $_A$L=Liquid, $_A$S=Solid. For Thermal $_B$(e) Linear Flex and Mechanical $_B$(E) Linear Flex, the relationships may respectively be stated as:

$_B L_e$ = Circumference = $\pi \cdot {_B D_e}$ and
$_B L_E$ = Circumference = $\pi \cdot {_B D_E}$.

Therefore, in a spherical bead the
Thermal Diameter = $_B D_e = {_B L_e}/\pi$; and the
Mechanical Diameter = $_B D_E = {_B L_E}/\pi$ Considering the thermal-mechanical response of the micro-bead thermocouple, the response may be predicted in terms of thermal-mechanical flex ($_BZ$) in relation to the illustrations found in FIGS. 5A-B.

More specifically, the Spherical Bead ($_B$) Thermal Flex is characterized as:

$$\text{Diameter } \Delta_B D_T \approx {_B D_{0T}}[1+(_B De \cdot \Delta_B T)]$$

$$\text{Area } \Delta_B A_T \approx {_B A_{0T}}[1+(2 \cdot {_B De} \cdot \Delta_A T)]$$

$$\text{Volume } \Delta_B V_T \approx {_B V_{0T}}[1+(3 \cdot {_B De} \cdot \Delta_A T)]$$

where $_B T_{Afinal} - {_B T_{Aactual}} = \Delta_B T_{Arange}$, and $$_B D_e = {_B C_{e@T=0}} + (m_B De \cdot {_B T_{actual}})$$

where $_B Ce_{@T=0}$ = 0.000006 In/in/° F.

$m_B e$ = 0.000 000 0023"/° F.

therefore at $_B T_{eactual}$ = 0° F., $_B T_e$ = 0.000006 in./° F./in.
and $_B T_{actual}$ = 900° F., Ta = 0.0000087 in./° F./in.
0.000006" + 2.07×10$^{-6}$ And, the Spherical Bead ($_B$) Mechanical Flex is characterized as:

$$_B \Delta D_E = (_B D_0 \cdot {_A F_{G,L,S}}) / (_B A_{E0} \cdot {_B D_E}) \quad \text{With} \quad _A F_{G,L,S} = {_A P_{G,L,S}} \times {_B A_{E0}}$$

$$_B \Delta D_B = (_B D_0 \cdot {_A P_{G,L,S}}) / (_B D_E)$$

therefore strain of enclosing substance $_A P_{G,L,S} = {_B D_E} \cdot (_B \Delta D_B / {_B D_0})$
where $_B \Delta D_E = {_B C_{@T=0}} + (_B E \cdot {_B T_{Eactual}})$
$_A F_G, {_A F_L}, {_A F_S},$ <==enclosing matter on sensor bead
where $_B D_{E@T=0}$ = 30,000,000 #/In$^2$ and $m_B De$ = (25,000,000 − 30,000,000 #/In$^2$) = −(5,000,000/ 900° F.) $\cdot {_B T_{actual}}$ where $_B D_{E@T=900}$ = 30,000,000 #/In$^2$ − 5,000,000 #/In$^2$ = 25,000,000 #/In$^2$ Having described the general nature of the system and the micro-bead itself, attention is turned to the method for concurrently sensing a combined temperature and pressure of a process. Referring to FIG. 5, in one embodiment, process 500 comprises sensing a plurality of cycles of the process (industrial, biological, natural, etc.) using a micro-bead sensor in direct contact with an element of the process (510), including providing a sensor consisting of two dissimilar metal wires terminated by a generally-spherical, micro-bead junction suitable for exposure to the process. Providing a sensor consisting of two dissimilar metal wires includes a termination process such as: welding; laser welding; friction welding; electron beam welding; and fusing.

As noted previously, the micro-bead junction may be most responsive to the variations of temperature and pressure of the process if left in an exposed state. However, the current disclosure contemplates the micro-bead sensor being protected in a manner that also permits accurate response to changes in temperature and pressure. For example, the sensor may be covered with a flexible, biologically-non-reactive coating suitable for exposure to processes of living organisms (e.g., latex, Next, at 514, the micro-bead junction of the sensor is exposed to the process, where in the junction senses the process and produces a signal in response to the process. The output signal is then received (518) by an interface or similar circuitry suitable for periodically capturing the emf voltage generated by the sensor.

Once the emf output signal has been received, it may be converted to digital data representing at least temperature and pressure using at least one reference point against which the sensor was calibrated as reflected in 522 and as described in more detail above relative to FIG. 1. Subsequently, the converted and reference point adjusted signals (e.g., temperature and pressure) are at least temporarily, stored in a memory (526). The operation of the method depicted in FIG. 5 preferably occurs during a time period short enough to permit the sensing and receiving of the signal to occur at a rate less than one-half of the period of any process cycle so as to avoid missing the process cycle. Further contemplated is a method wherein the rate of sensing and receiving the signal is less than one-tenth of the average process cycle so that even minor variations in the timing and sequence of the cycle may be accurately detected and characterized.

As noted above, the disclosed method may have particular applicability to a manufacturing process employing a mold and where the sensor is applied to the mold at a location such as a mold cavity vent; in contact with the material being molded; an aperture through which molding material flows; a mold flow controlling mechanism; an ejector pin; a mold cavity; a stationary pin; machine nozzle retaining hole; and a mold cavity plate. Considering a biological process, such as monitoring the temperature, blood pressure, pulse, respiration or other processes of a living organism, the sensor would be applied to the living organism to sense aspects of the biological process(es). Such processes may require a sensor to be attached for: epidermal skin pressure contact; capillary (under/inner skin) contact; blood vessel contact; vascular inner blood vessel transmission contact; and inner fluid vessel structure membranes.

As described above, converting the signal to data representing at least temperature and pressure, operation 522, results in a first output representing a digital temperature change ($T_{emf}$) and a second output representing a pressure change ($P_{emf}$) due to bead compression, where a sum of the signals represents the combination of the temperature change and pressure change from the at least one reference point. When the reference point temperature and pressure are both below the temperature and pressure of the process aspects being sensed, the temperature change and pressure change would both be reflected as positive or increasing. It is further contemplated that the relative and/or changing pressure component can be representative of the specimen's blood pressure or other biological pressure. To sense pressure aspects of the biological process reaches an ambient material may be used to cover and hold the sensor adjacent to the specimen's skin. The rising vascular pressure adds a $+P_{emf}$ to reach the systolic maximum pressure pulse point and falls to the lower diastolic $-P_{emf}$ point. The blood flow rate resulting from the heart pulses is also able to be read as the peak points without the standard cuff used to stop the blood flow and cause an increase in blood pressure. Such an embodiment is represented as a "wrist cuff" device of FIG. 2. For example, referring to FIG. 2, there is depicted a remote, self-contained blood-pressure sensor 610 that may be applied to a specimen's forearm (wrist) or similar location. The sensor includes a housing 612 that encompasses components of the circuitry described above, but in this embodiment is capable of regularly receiving signals from a plurality or array of micro-bead sensors 620a and 620b. The array of sensors detect temperature and pressure changes as described above, and the array may include two or more "lines" of between about ten and twenty, or more, regularly-spaced sensors. In one version of the depicted embodiment, a resilient or spring-like member 630 is employed in a slightly convex configuration to assure that when worn by a specimen, the thermocouple junctions remain in proximity to or in contact with the skin and an underlying artery. Lastly, the housing and sensors are attached to the specimen's arm using an arm or wrist band 640, where the ends of the band may be connected when in use via hook and loop type fastener (e.g., Velcro™), snaps or similar disengageable fasteners not shown). Signals may be received and sent to an interface as depicted or may be wirelessly transmitted.

It will be appreciated that various of the disclosed embodiments and other features and functions, or alternatives thereof, may be desirably combined into many other different systems or applications. Also, various presently unforeseen or unanticipated alternatives, modifications, variations or improvements therein may be subsequently made by those skilled in the art which are also intended to be encompassed by the following claims.

What is claimed is:

1. A method for concurrently sensing a combined temperature and pressure of a process over time, using a single sensor, comprising:
    sensing a plurality of cycles of the process using a single micro-bead sensor in direct contact with a flow of a material in the process, including placing a sensor consisting of two dissimilar metal wires terminated by a generally-spherical, micro-bead junction in a path of the flowing material;
    exposing the micro-bead junction to the process, wherein the micro-bead junction is responsive to material flow in the process and produces a signal in response to the process;
    receiving the signal;
    converting the signal to data representing at least temperature and pressure using at least one reference point against which the sensor was calibrated; and
    at least temporarily, storing data representing the temperature and pressure in memory; wherein the sensing and receiving of the signal occurs at a rate less than one-half that of a period of the process cycle.

2. The method according to claim 1, wherein the rate of sensing and receiving the signal is less than one-tenth of the average process cycle.

3. The method according to claim 2, wherein converting the signal to data representing at least temperature and pressure in produces a first output representing a digital temperature change ($T_{emf}$) and a second output representing a pressure change ($P_{emf}$) due to bead compression relative to the at least one reference point, where a sum of the signals represents the combination of the temperature change and pressure change from the at least one reference point.

4. The method according to claim 3, wherein the reference point temperature and pressure are both below the temperature and pressure of the process aspects being sensed and where the temperature change and pressure change are both positive.

5. The method according to claim 2, wherein the rate of sensing and receiving the signal is less than one-tenth of an average process cycle and where variations in the timing and sequence of the cycle are accurately detected.

6. The method according to claim 1, wherein the process is a manufacturing process employing a mold and where the sensor is applied to the mold at a location selected from the group consisting of:
    a mold cavity vent;
    a slot in the mold;
    in contact with the material being molded;
    an aperture through which molding material flows;
    a mold flow controlling mechanism;
    an ejector pin;
    a mold cavity;
    stationary pin;
    machine nozzle retaining hole; and
    a mold cavity plate.

7. The method according to claim 1, wherein providing a sensor consisting of two dissimilar metal wires includes a termination process selected from the group consisting of:
    welding;
    laser welding;
    friction welding;
    electron beam welding; and
    fusing.

8. The method according to claim 1, further comprising producing the generally-spherical, micro-bead junction of the sensor wherein sensitivity of the micro-bead junction is inversely related to a diameter of the micro-bead.

9. The method according to claim 1 wherein the micro-bead junction is at least partially covered with a flexible coating prior to exposure to the cyclic process.

10. A system to concurrently measure at least temperature and pressure of a cyclic process using a common sensor, comprising:
    at least one sensor consisting of a generally spherical micro-bead junction formed from dissimilar metals, said micro-bead sensor being exposed to material flowing in the process, wherein the sensor produces a signal in response to the flow of material in the process;
    electrical circuitry to receive a sensor output signal and convert the sensor output signal to a digital signal;
    a processor for receiving the digital signal and processing the received digital signal in order to quantify at least temperature and pressure components of the signal relative to at least one reference point against which the sensor was calibrated, the processor correcting for the reference point to produce an output representing at least two parameters.

11. The system according to claim 10, wherein said processor, using the at least one reference point, produces a first output representing a digital temperature change ($T_{emf}$) and a second output representing a pressure change ($P_{emf}$) due to bead compression wherein a sum of the $T_{emf}$ and $P_{emf}$ represents the combination of the temperature change and pressure change determined relative to the at least one reference point.

12. The system according to claim 10, wherein a sensitivity of the micro-bead junction is inversely related to a diameter of the micro-bead.

* * * * *